United States Patent

Gilchrist et al.

[11] Patent Number: 6,143,318
[45] Date of Patent: Nov. 7, 2000

[54] ANTIMICROBIAL COMPOSITION COMPOSED OF CONTROLLED RELEASE GLASSES

[75] Inventors: Thomas Gilchrist; David Michael Healy, both of Ayr, United Kingdom

[73] Assignee: Giltech Limited, Ayr, United Kingdom

[21] Appl. No.: 08/875,865

[22] PCT Filed: Feb. 6, 1996

[86] PCT No.: PCT/GB96/00267

§ 371 Date: Aug. 6, 1997

§ 102(e) Date: Aug. 6, 1997

[87] PCT Pub. No.: WO96/24364

PCT Pub. Date: Aug. 15, 1996

[30] Foreign Application Priority Data

Feb. 6, 1995 [GB] United Kingdom .................. 9502253

[51] Int. Cl.$^7$ ...................................................... A61N 9/70
[52] U.S. Cl. ........................... 424/446; 424/404; 424/405; 424/406; 424/409; 424/421; 424/445; 424/617; 424/618; 424/630; 424/642; 424/722; 424/78.06; 514/494; 514/495; 514/500
[58] Field of Search ..................... 424/445–449, 424/405, 404, 406, 409, 411, 421, 417, 618, 630, 641, 642, 617, 722, 78.06, 78.07, 78.02; 514/492, 494, 495, 499, 500

[56] References Cited

U.S. PATENT DOCUMENTS 5,180,585  1/1993  Jacobson et al. ........................ 424/405
5,470,585  11/1995  Gilchrist .................................. 424/604

FOREIGN PATENT DOCUMENTS 2163346  2/1986  United Kingdom .
2164557  3/1986  United Kingdom .

OTHER PUBLICATIONS

Derwent English Abstract of Japanese Patent Application 01/317133.
Derwent English Abstract of Japanese Patent Application 02/258256.
Derwent English Abstract of Japanese Patent Application 05/001226.
Derwent English Abstract of Japanese Patent Application 03/146436.
Patent Abstract of Japan; Publication No. JP6080527; Publication Date Mar. 22, 1994; Appli. No. JP920257364; Appli. Date Aug. 31, 1992 by Katsuhiro et al. for Antimicrobial Agent.
Söderberg et al., The Effects of an Occlusive Zinc Medicated Dressing on the Bacterial Flora in Excised Wounds in the Rat, from Infection, vol. 17, 1989.
Schmidt–Lorenz, from Hygiene & Medizin, Sep. 1981, pp. 389–398, with English language Summary.
Sheridan et al., The Effect of Antibacterial Agents on the Behaviour of Cultured Mammalian Fibroblasts, from Journal of Materials Science, vol. 6, 1995, pp. 853–856.

*Primary Examiner*—Neil S. Levy
*Attorney, Agent, or Firm*—Ratner & Prestia

[57] ABSTRACT

There is provided an antimicrobial composition for combatting infections. The material is a controlled release glass having two or more agents selected from the group consisting of metals, selenium and boron. Preferably the agents are selected from the group consisting of copper, silver, magnesium, zinc, cerium,consisting of copper, silver, magnesium, zinc, cerium, manganese bismuth, selenium and boron. The combinations of copper and silver and of copper and zinc are particularly preferred and exhibit synergist activity. The antimicrobial composition is effective against infections due to Proteus spp.

7 Claims, 8 Drawing Sheets

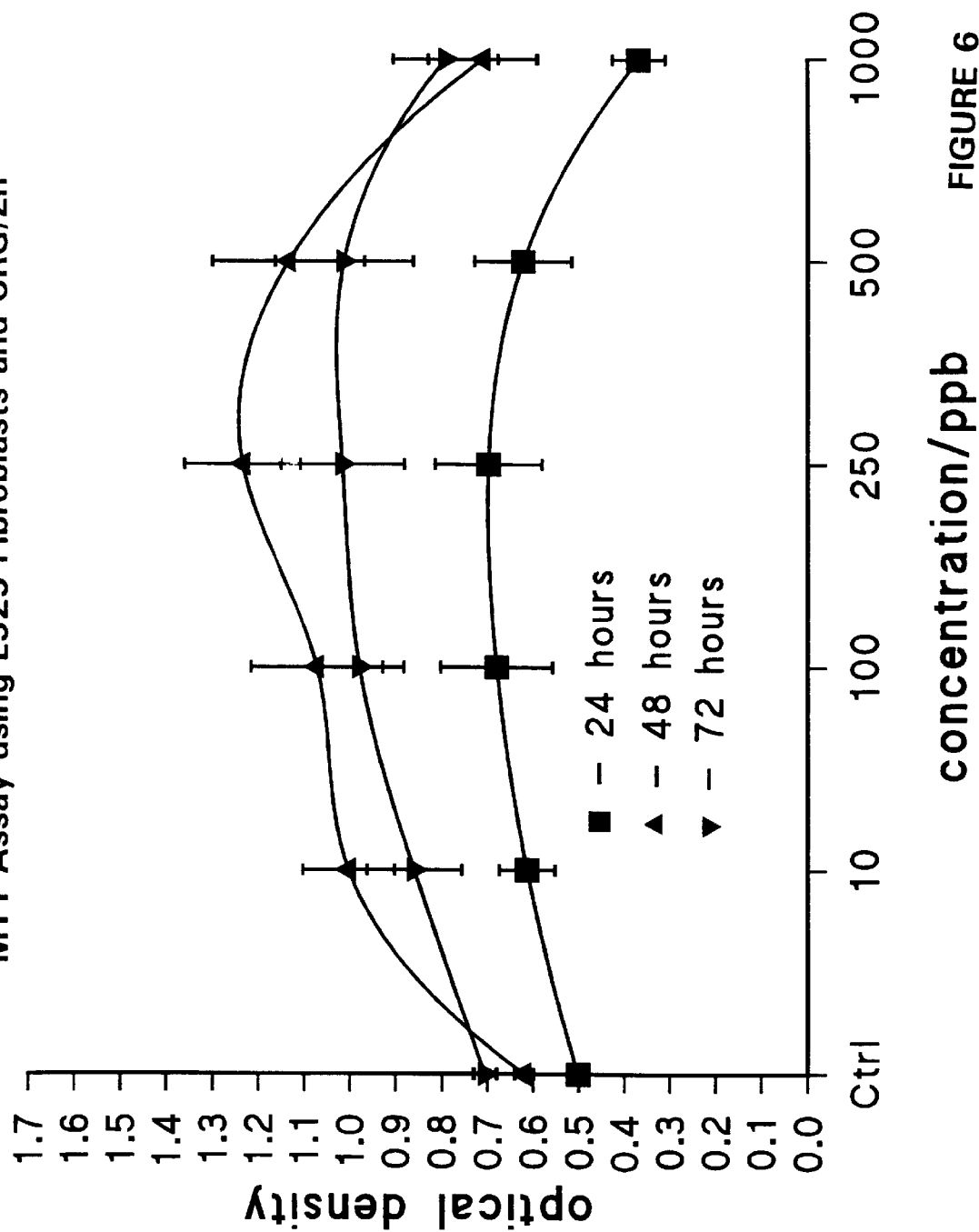

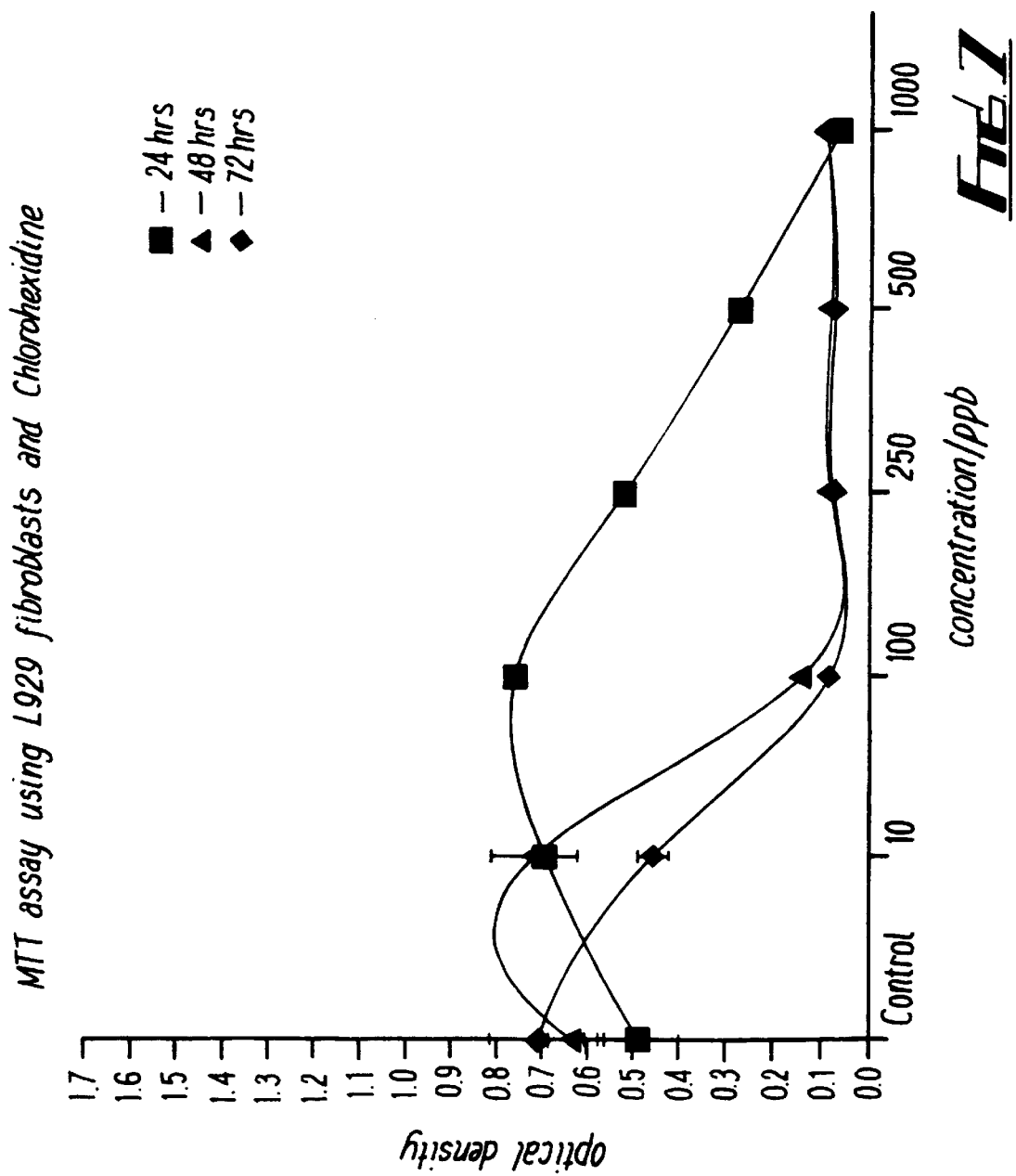

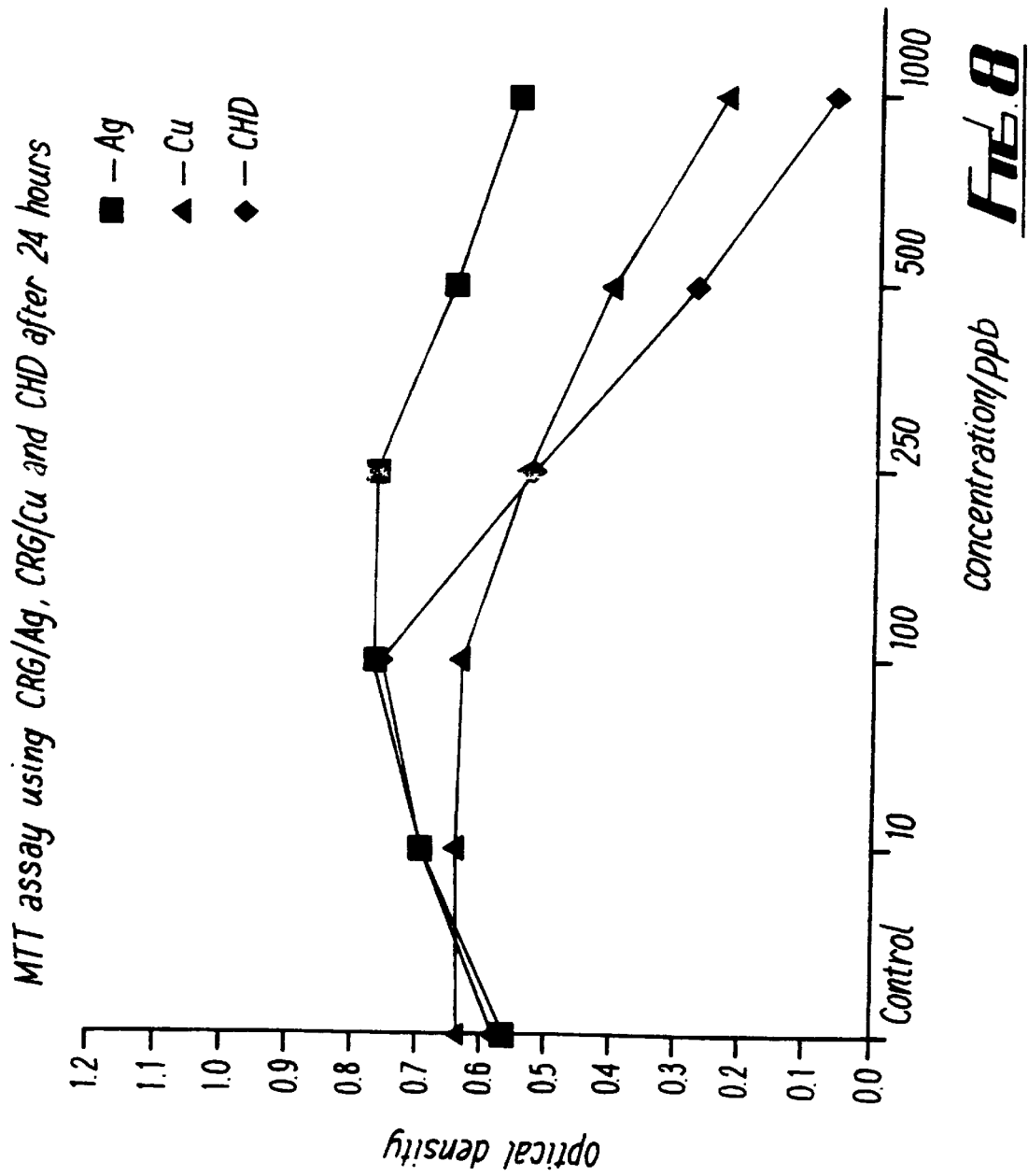

ANTIMICROBIAL COMPOSITION COMPOSED OF CONTROLLED RELEASE GLASSES

The present invention relates to an antimicrobial material for combatting infections.

To combat infections at wound sites a variety of antibacterial agents have been incorporated into wound dressings. Some of these agents have been shown to have a deleterious effect on the delicate environment of a healing wound and may indeed retard the rate of wound healing. Individually, silver and copper are known to have useful biocidal properties (see Pyle et al, J. Appl. Bacteriology 1992. vol. 72, no.1, pp 71–79).

The use of glasses which can dissolve in water and body fluid and which are applied internally of the body are well-known. These glasses are formed from phosphorus pentoxide and may be modified to dissolve over a period of minutes, months or even years, as required. To date, such glasses have been used, in medicine, for the controlled release of a number of agents, for example, drugs, hormones and trace elements, but in each case the glass has been applied internally of the body to allow the agent to leach out into the body's circulatory system.

It is known that certain glasses, in which the usual glass former, silicon dioxide, of traditional glasses is replaced with phosphorus pentoxide as the glass former, are soluble in water and body fluids. The rate of dissolution is controlled largely by the addition of glass modifiers such as calcium oxide. In simple terms, the greater the concentration of the modifier the slower is the rate of dissolution. The rates of dissolution which can be imparted to the glasses may range from minutes to months or even to several years. Soluble phosphate based glasses which have demonstrated good biocompatibility can incorporate inorganic metals such that a sustained release of the metals can be provided at the wound site.

Controlled release glasses (CRGs) which release silver ions to combat infections as described in WO-A-90/08470 of Giltech Limited, for example.

It has now been found that a combination of metal ions can, if suitably presented, reduce the amount of antimicrobial metal ions required to achieve bacteriostatic or bactericidal activity, whilst at the same time lowering the inflammatory response of the tissue.

The present invention therefore provides a method of combatting infection in a wound (such as microbial or fungal infection, for example bacterial, viral, or fungal infection) whilst maintaining cell viability, said method comprising providing a controlled release glass containing a combination of two or more agents selected from the group consisting of metals, selenium and boron. The agents are selected and combined together in concentrations sufficient to achieve bacteriostatic or bactericidal benefit. The concentrations of each agent is low enough to avoid cell death in the healing wound (for example due to protein binding etc) but in combination is sufficient to achieve at least bacteriostasis. By careful selection of the combination of agents used infection can be combatted and wound healing promoted. In one embodiment the agents are selected from the group consisting of copper, silver, magnesium, zinc, cerium, manganese, bismuth, selenium and boron. Preferably at least one agent is silver, boron, bismuth, manganese, copper, cerium or zinc.

The present invention also provides a controlled release glass (CRG) composition for combatting infection in cells (such as microbial or fungal infection, for example bacterial or viral infection, including parasitic infections, for example bilharzia and blue/green algae) whilst maintaining cell viability. The glass controllably releases quantities of at least two agents selected from the group consisting of metals, selenium and boron; the combined concentration of released agents being sufficient to combat infections whilst aiding wound healing.

The controlled release glass according to the present invention comprises the agents set out above and in one embodiment the agents are selected from the group consisting of copper, silver, magnesium, zinc, cerium, manganese, bismuth, selenium and boron. Glasses containing silver as one agent are especially preferred. In particular combinations of copper and silver have been found to be particularly efficacious. Alternatively a glass containing combinations of copper and zinc or of magnesium and zinc are also suitable. Controlled release glasses of the type described in WO-A-89/01793 and WO-A-90/08470 are suitable as a means of presenting the agent combination.

The present invention also provides the use of a controlled release glass as described above in the manufacture of a medicament for combatting infection in cells (such as microbial or fungal infection, for example bacterial or viral infection) whilst maintaining cell viability.

According to one embodiment of the present invention, the water-soluble glass comprises an alkali metal oxide $M_2O$, an alkaline earth oxide MO, phosphorus pentoxide $P_2O_5$ and said agents, for example silver and copper in elemental or salt form.

Most preferably, said glass contains not more than 40 mole % $M_2O$ or MO, not less than 10 mole % $M_2O$ or MO, and not more than 50 mole % nor less than 38 mole % phosphorus pentoxide, with the inclusion of 0.05 to 5.0 mole % of said agents (for example a silver salt, copper salt, magnesium salt and/or copper salt).

Said alkali metal oxide may be sodium oxide ($Na_2O$), potassium ($K_2O$) or a mixture thereof; and said alkaline earth oxide may be calcium oxide (CaO), magnesium oxide (MgO), or a mixture thereof.

The glass may also contain less than 5 mole % silicon dioxide ($SiO_2$), boric oxide ($B_2O_3$), sulphate ion ($SO_4^{2-}$) a halide ion, copper oxide (CuO) or a mixture thereof.

Typically the soluble glasses used in this invention comprise phosphorus pentoxide ($P_2O_5$) as the principal glass-former, together with any one or more glass-modifying non-toxic materials such as sodium oxide ($Na_2O$), potassium oxide ($K_2O$), magnesium oxide (MgO), zinc oxide (ZnO) and calcium oxide (CaO). The rate at which the glass dissolves in fluids is determined by the glass composition, generally by the ratio of glass-modifier to glass-former and by the relative proportions of the glass-modifiers in the glass. By suitable adjustment of the glass composition, the dissolution rates in water at 38° C. ranging from substantially zero to 25 mg/cm²/hour or more can be designed. However, the most desirable dissolution rate R of the glass is between 0.01 and 2.0 mg/cm²/hour. The water-soluble glass is preferably a phosphate glass. Silver may advantageously be introduced during glass manufacture as silver orthophosphate ($Ag_3PO_4$). The content of silver and other agents in the glass can vary in accordance with conditions of use and desired rates of release, the content of silver and other agents generally being up to 5 mole %. While we are following convention in describing the composition of the glass in terms of the mole % of oxides, of halides and of sulphate ions, this is not intended to imply that such chemical species are present in the glass nor that they are used for the batch for the preparation of the glass.

Boron may be present as a glass former within the glass itself, partially replacing phosphorus pentoxide. Generally the agents are added to the glass composition during glass manufacture, ie. in the melt. Alternatively, the glass may be preformed and the agent then introduced thereto.

The glass may be formed by a number of methods. It may simply be cast by conventional or centrifugal procedures, or it may be prepared via one or more stages of rod, fibre or tube drawing. Other preparation techniques include foamed glass or comminution of the glass followed by pressing and sintering into a solid body. It may be presented for example as a solid body, a powder or granules of preselected size, as flakes, or in the form of a number of hollow cylinders.

The glass composition according to the present invention may be used in any suitable form and mention may be made of powders, sinters, rods, sheets, beads and the like. Where the glass is to be used in finely divided form, it is possible for an admixture of two glasses to be prepared, each containing a single agent, and then to be combined in admixture to produce the composition according to the present invention. In one embodiment the glass may be in the form of a powder, as granules, as fibres that can be woven into a dressing form, as a sinter which may be shaped in a particular way, or cast into the required shape eg a collar to surround the area of penetration of a catheter into the body.

When combined with a carrier the glass may be used as a filler in polymers for surface release eg in silicones, natural and synthetic rubbers and medical plastics and polymers.

Alternatively, the glass may be incorporated in the adhesive of adhesive film dressings, in lint, wool, tow and gauze dressings and as part of wound management products such as foam, hydrogels and hydrocolloids, films, gels and creams.

Combinations of these examples can also be used.

The present invention will now be further described with reference to the following, non-limiting, examples.

BRIEF DESCRIPTION OF DRAWINGS

FIG. 6 is a graph showing the cytotoxicity by MTT assay on L929 fibroblast of controlled release glass containing Zn at various concentrations at 24, 48 and 72 hours, FIG. 7 is a graph showing the cytotoxicity by MTT assay on L929 fibroblast of CHD at various concentrations at 24, 48 and 72 hours.

EXAMPLE 1

Figure 1:
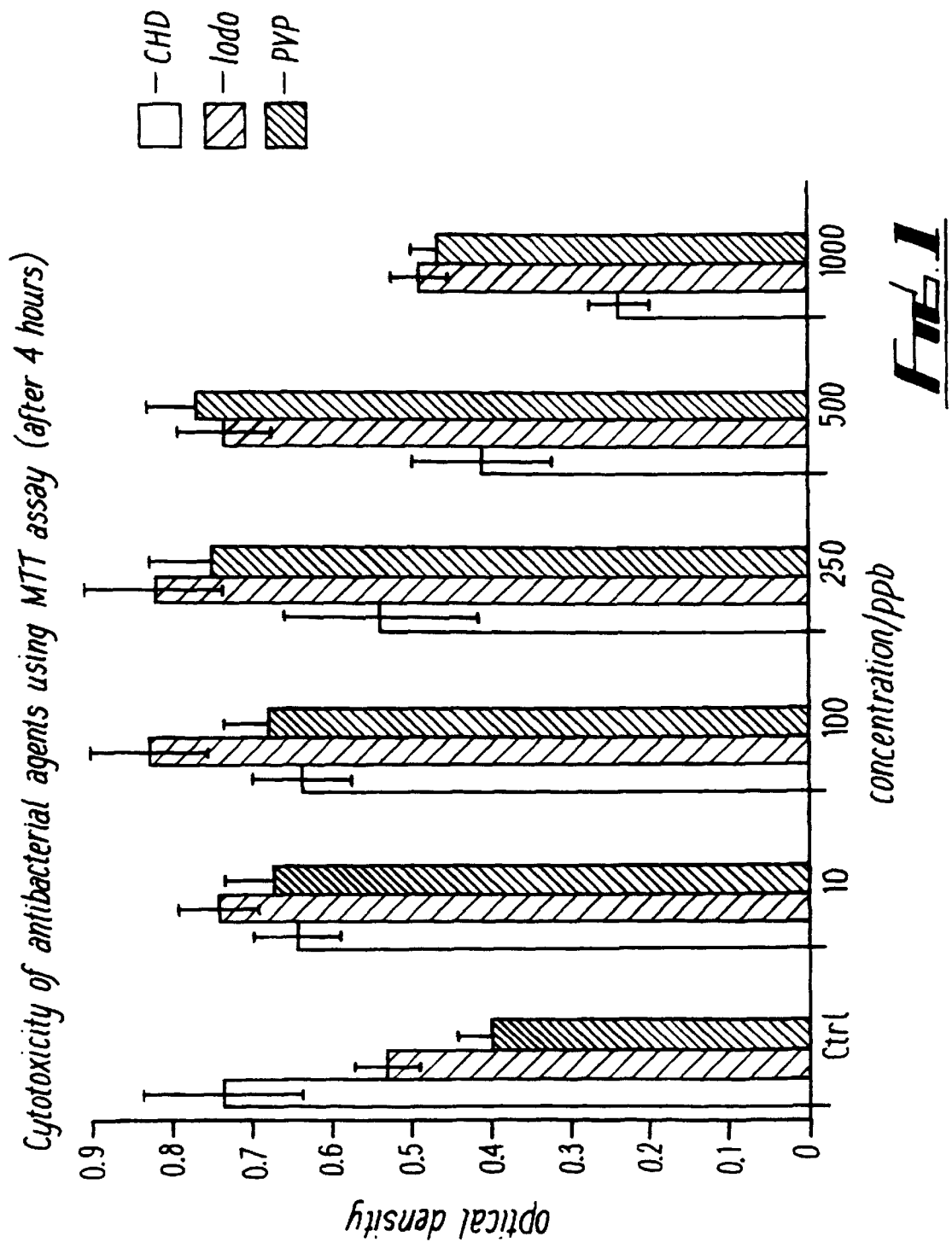
FIG. 1 is a graph showing the cytotoxicity by MTT assay of the antibacterial agents CHD, iodine and PVP at various concentrations after 4 hours.

In this study a comparison of the in vitro cytotoxic effect of various antibacterial agents is made by means of mammalian cell culture with MTT (3-(4,5-dimethylthiazol-2-yl)-2,5,-diphenyltrazolium bromide) assay.

Materials and Methods

The materials used were controlled release glasses containing silver, copper, magnesium and zinc ions, chlorhexidine diacetate salt (CHD), Iodoform (0.9 wt % iodine) and polyvinylpyrrolidone iodine complex with 11.4% available iodine (PVP). It has been shown that the biocidal effects of silver, copper and iodine occur at the levels of 10, 110 and 200 parts per billion (ppb) respectively. A range of exudates/solutions were prepared in the following concentrations, 1, 10, 100, 250, 500 and 1000 ppb, with sterile distilled water and double strength cell culture medium.

The L929 mouse fibroblasts were placed in 96 well plates, each well containing $1 \times 10^5$ cells suspended in $200 \mu l$ of cell culture medium with 5% foetal calf serum, and incubated at 37° C./5% carbon dioxide for 48 hours. The cell culture medium was removed and replaced with the prepared exudates/solutions. The control was a solution of 50% double strength cell culture medium and 50% sterile (PBS). The plates were then incubated for time periods of 24, 48 and 72 hours following which the MTT assay was carried out using a standard procedure.

Results

After 24 hours, apart from chlorhexidine (CHD), no material had a deleterious effect on the growth of the cells up to a concentration of 1000 ppb. The controlled release glasses containing Cu, Mg and Zn ions all seem to have the effect of increasing the metabolic rate of the cells after 48 hours and the effect is seen further at 72 hours with Cu at all levels above 10 ppb.

With increasing time the CHD causes cell death at just 100 ppb. The Ag releasing glass inhibited cell growth at 48 hours but after a further 24 hours the number of viable cells present is comparable with the other ion releasing glasses. The detrimental effect of Iodoform and PVP on cell activity is not seen until 1000 ppb and upto this point resemble the profile of the Ag glass.

Conclusion

It can be seen that the controlled metal ion releasing glasses sustain cell growth, if not increase the rate of cell division, whereas the antibacterial agent chlorhexidine produces irreversible cell damage at low concentrations.

As the glasses are releasing the metal ions they will become available over a period of time and therefore the levels of the ions will be lower initially. This may explain why the Cu and Ag ions did not kill all the cells at 1000 ppb.

EXAMPLE 2

The MTT assay is now widely used in the evaluation of biomaterials, and is becoming the standard in vitro test method for use in examining extracted or soluble samples.

The cell line used for this study was the established L929 mouse fibroblast, grown in standard culture medium supplemented with 10% foetal calf serum.

The following materials were examined

Materials used: CRG/Ag

CRG/Cu

Chlorohexidine (CHD)

Polyvinylpyrolidone (PVP)

Iodoform

The compositions of the silver and copper glasses (CRG/Ag and CRG/Cu respectively) were as follows:

|  | Component | Mole % |
|---|---|---|
| Silver Glass (CRG/Ag): | | |
| | $Na_2O$ | 34 |
| | CaO | 15 |
| | $Ag_2O$ | 3 |
| | $P_2O_5$ | 48 |
| The solution rate was 2.74 mg/cm²/hour at 37° C. | | |
| Copper Glass (CRG/Cu): | | |
| | $Na_2O$ | 32 |
| | CaO | 15 |
| | CuO | 5 |
| | $P_2O_5$ | 48 |
| The solution rate was 1.54 mg/cm²/hour at 37° C. | | |

The antiseptic agents and controlled release glasses were added to sterile distilled water to give a concentration of 2000 ppb, and stored before use 4° C.

The fibroblast cells were suspended in culture medium and aliquoted into 96 well plates, to a cell density of approximately 50,000 cells/mL, 500 µL were placed in each well. The plates were incubated for 2 days at 37° C. to near confluence.

After this time period dilutions of all materials were prepared at concentrations of 1000, 500, 250, 100, 10 and 1 ppb with cell culture medium. The original cell culture medium was removed from the plates and 100 µL/well of these dilutions were added to each plate as detailed below. Controls were prepared from 1 part double strength cell culture medium to 1 part sterile PBS.

The solutions were incubated with the cells for 24 hours at 37° C. After this time period the MTT salt was prepared at a concentration of 5 mg/ml. The material dilutions were removed from the plates and 100 µL/well of MTT salt added. The plates were then incubated for 4 hours. During this period viable cells will clause a reduction of tetrazolium to formazan producing a blue crystal formation. Thus the intensity of the blue is directly related to the number of activity of the cells. The MTT solution was then removed and 50 µL/well of isopropanol was added to each plate and left for 20 minutes. The isopropanol is used to release the dye which was formed within the viable cells.

Figure 2:
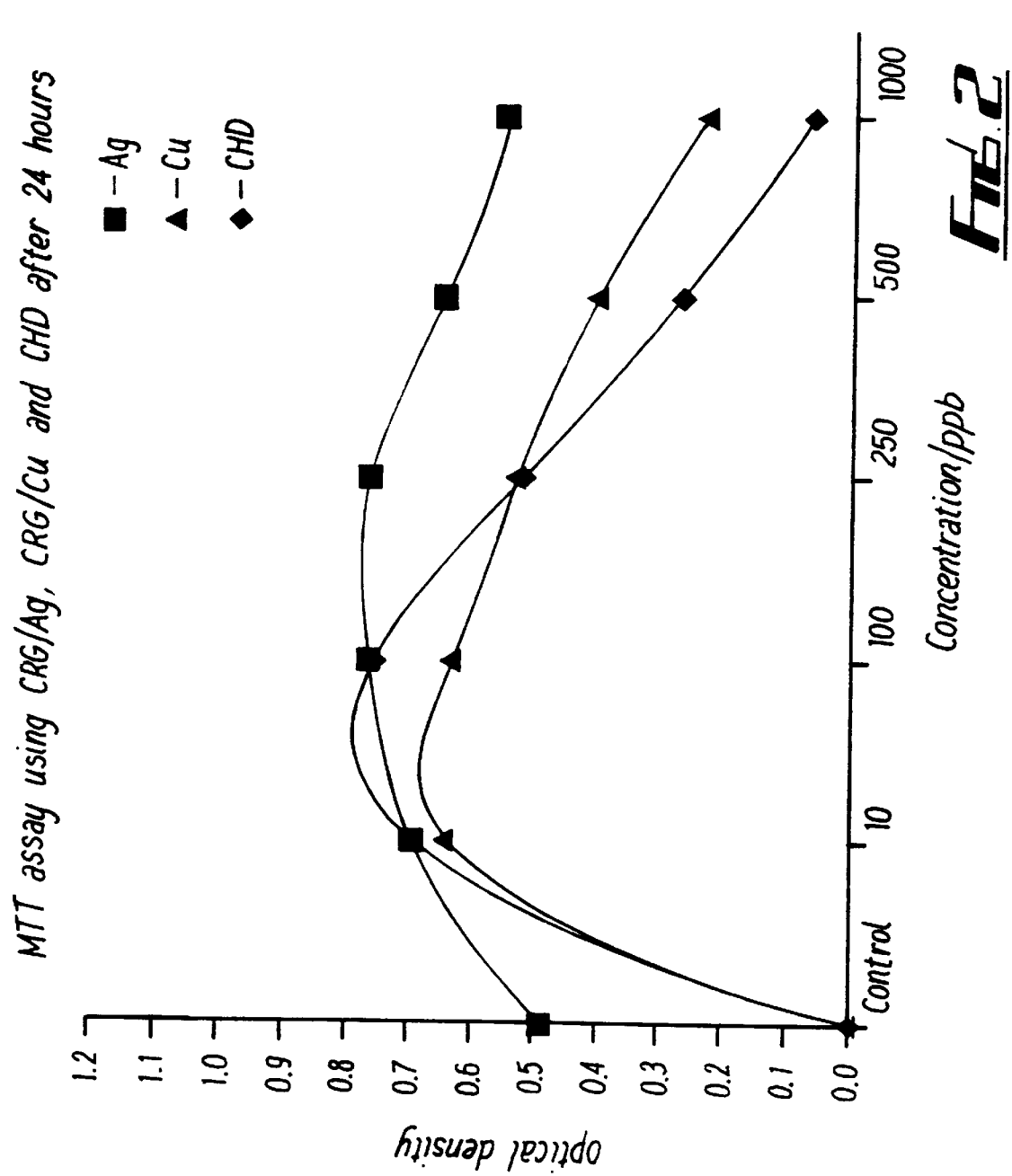
FIG. 2 is a graph showing the cytotoxicily by MTT assay of CHD and controlled release glass containing Cu or Ag at various concentratios after 24 hours.
Figure 3:
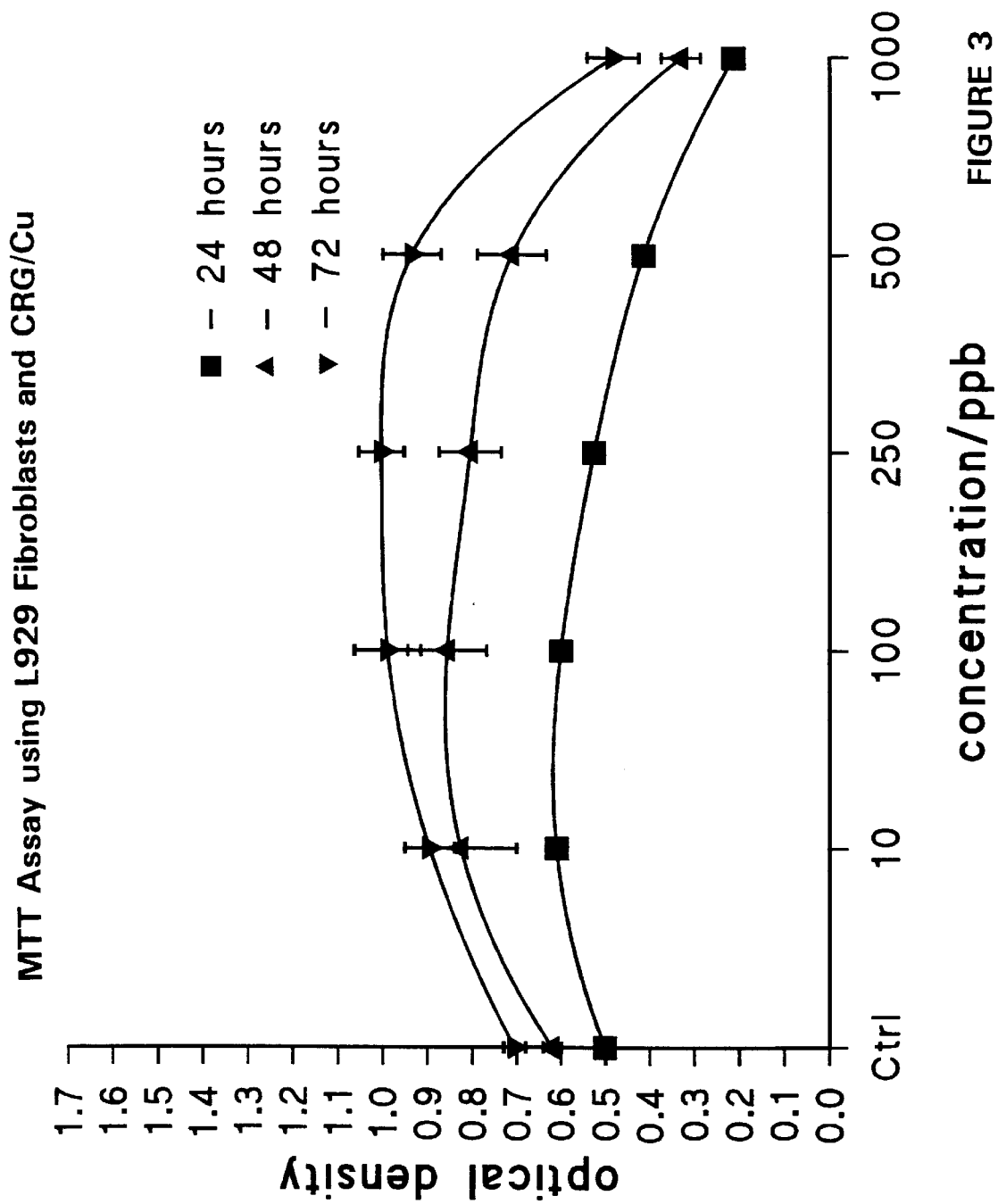
FIG. 3 is a graph showing the cytotoxicity by MTT assay of controlled release glass containing Cu at various concentrations after 24, 48 and 72 hours.
Figure 4:
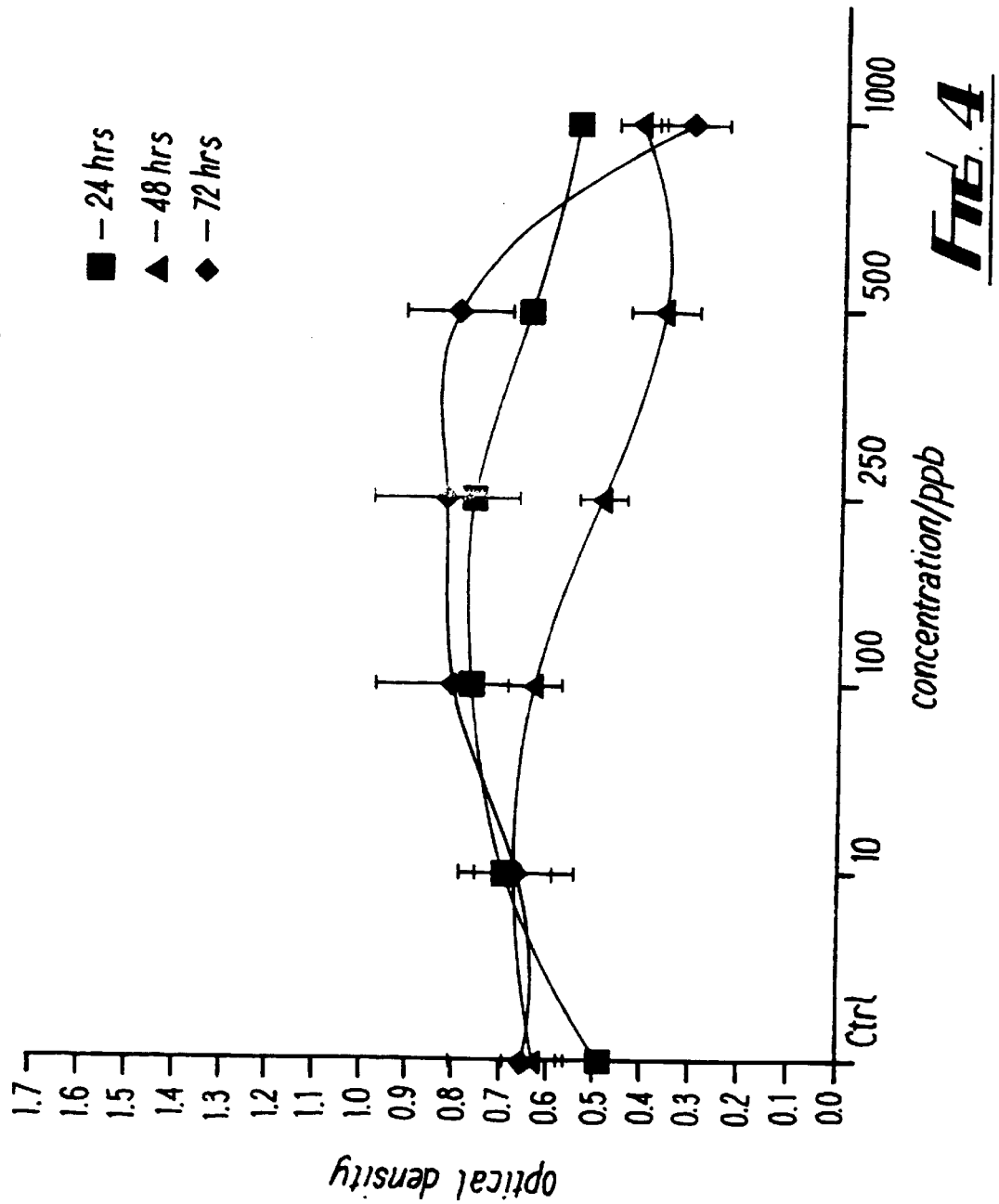
FIG. 4 is a graph showing the cytotoxicity by MTT assay of controlled release glass containing Ag at various concentrations after 24, 48 and 72 hours.
Figure 5:
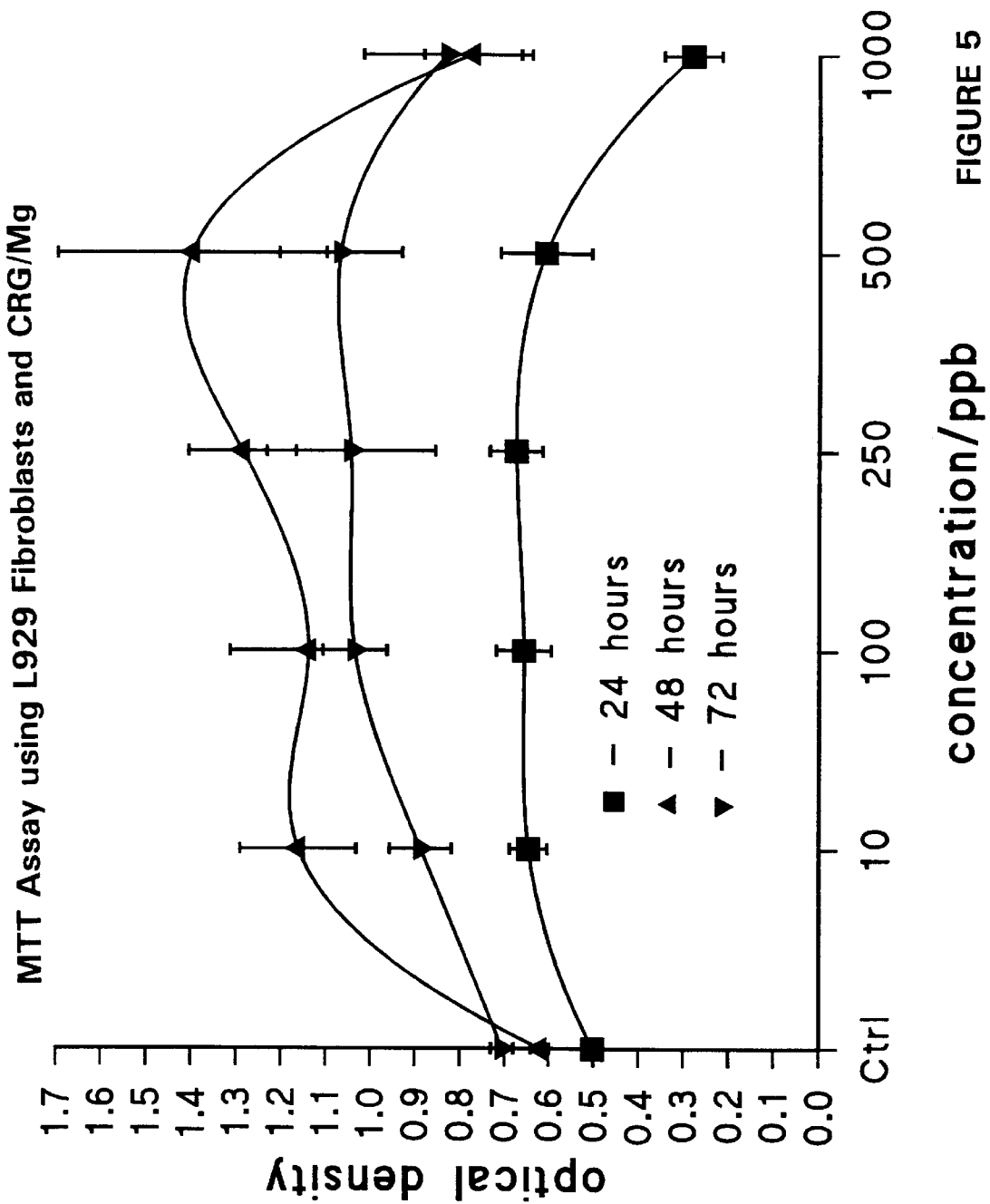
FIG. 5 is a graph showing the cytotoxicity by MTT assay on L929 fibroblast of controlled release glass containing Mg at various concentrations at 24, 48 and 72 hours.

The optical densities of all the solutions in the plates were then measured using and ELISA plate reader. The results set out in FIG. 1 to 8 were obtained.

EXAMPLE 3

Glass compositions each containing a single agent of interest were individually tested against a range of microorganisms by placing a bead of the test glass in the centre of an agar plate which is then innoculated with bacteria to cultivate a continuous lawn. The size of the zone of inhibition produced around each sample was measured and recorded. The zone size is proportional to the antibacterial activity of each composition, since the agent present in the glass gradually diffuses out into the surrounding agar and affects bacterial growth in that area. It is expected that the active agents diffuse further than indicated by the outer edge of the zone, but in concentrations too low to cause antibacterial activity.

The sensitivity tests were conducted on isosens agar plates each with a standard depth of agar. The agar plates were used within 4 days of preparation and were stored in a cold room (4° C.) until use.

Glass compositions containing a metal ion (selected from silver, copper, magnesium and zinc) were prepared. The silver and copper glasses are as described in Example 2. Each glass was tested against the following microorganisms: *Candida albicans, Staphylococcus aureus, E. Coli, Pseudomonas areuginosa,* Enterococcus and a randomly selected strain of Proteus spp.

After 24 hours, 48 hours and 72 hours the zones were measured and the results are set out in Table 1.

TABLE 1

| Test Organism | Incubation Time (Hrs) | Zone Size (mm) | | | |
|---|---|---|---|---|---|
| | | Ag | Cu | Mg | Zn |
| Pneumococcus | 24 | 11 | 11 | NT | NT |
| | 48 | 8 | 10 | NT | NT |
| | 72 | 5 | 9 | NT | NT |
| Enterococcus | 24 | 2 | 6 | 0 | 0 |
| | 48 | 2 | 5 | 0 | 0 |
| | 72 | 0 | 4 | 0 | 0 |
| Staph aureus | 24 | 4 | 6 | 0 | 0 |
| | 48 | 3 | 6 | 0 | 0 |
| | 72 | 3 | 4.5 | 0 | 0 |
| Proteus sp. | 24 | 1.5 | 9 | 2 | 4.5 |
| | 48 | 1.5 | 8 | 2 | 0 |
| | 72 | 1.5 | 4 | 2 | 0 |
| E coli | 24 | 5 | 9 | 0 | 3 |
| | 48 | 3 | 8 | 0 | 2 |
| | 72 | 2 | 6 | 0 | 1 |
| Pseudomonas | 24 | 4 | 9 | 3 | 3 |
| | 48 | 3 | 7 | 2 | 0 |
| | 72 | 3 | 5 | 2 | 0 |
| Candida alb. | 24 | 3 | 5 | 0 | 2.5 |
| | 48 | 0 | 0 | 0 | 0 |
| | 72 | 0 | 5 | 0 | 0 |

Once the zone sizes were established, pairs of agents were tested together. The two beads of glass were placed a specific distance apart on a single prepared agar plate, the distance between the beads was the total of their respective zone sizes at 24 hours minus 2 mm. After 24 hours the microbial growth was examined. Particular attention was paid to the area where the zones of antibacterial activity converged. Here the area of microbial growth tapers down to a fine point. Where microbial growth between the beads was completely prevented it was concluded that the combination of agents had a synergistic action.

A combination of copper and silver and a combination of copper and zinc were found to exhibit enhanced activity, particularly against Proteus sp.

The Example was repeated, with the spacing of the beads being the sum of the respective zones sizes of the agents at 24 hours. The same combinations were found to be particularly effective, and the antibacterial activity observed was still evident after 72 hours.

What is claimed is:

1. A method of combatting infection in a wound whilst maintaining cell viability, said method comprising steps of:
    (a) providing a controlled release water soluble glass able to controllably release quantities of at least two agents, one of said agents being silver and the other of said agents being selected from the group consisting of copper, magnesium and zinc, or said two agents being copper and zinc, the combined concentration of the released agents being sufficient to combat infections whilst maintaining cell viability, said glass comprising an alkali metal oxide $M_2O$, an alkaline earth oxide MO and phosphorus pentoxide $P_2O_5$; and
    (b) incorporating said glass into dressings or into a wound management product and placing said dressing or said management product onto the wound.

2. A method as claimed in claim 1 wherein said infection is due to Proteus spp.

3. A method as claimed in claim 1, wherein said agents are silver and zinc.

4. A method as claimed in claim 1, wherein said agents are silver and magnesium.

5. A method as claimed in claim 1, wherein said agents are zinc and copper.

6. A method as claimed in claim 1, wherein said agents are silver and copper.

7. A method as claimed in claim 1, wherein the content of each of said agents is more than 0 mole % and up to 5 mole %.

* * * * *